United States Patent
Leese et al.

(10) Patent No.: US 6,767,718 B2
(45) Date of Patent: Jul. 27, 2004

(54) LIPODEPSIPEPTIDE ANTIBIOTICS AND METHODS OF PREPARATION

(75) Inventors: Richard A. Leese, Suffern, NY (US); William V. Curran, Pearl River, NY (US); Donald B. Borders, Suffern, NY (US)

(73) Assignee: BioSource Pharm, Inc., Spring Valley, NY (US)

( * ) Notice: Subject to any disclaimer, the term of this patent is extended or adjusted under 35 U.S.C. 154(b) by 0 days.

(21) Appl. No.: 10/142,303

(22) Filed: May 10, 2002

(65) Prior Publication Data

US 2003/0224475 A1 Dec. 4, 2003

(51) Int. Cl.$^7$ .......................... A61K 38/15; C07K 1/06; C07K 11/00; C12P 21/04
(52) U.S. Cl. ................ 435/68.1; 435/71.3; 514/11; 530/323; 530/327; 530/328; 530/336; 530/343; 530/345
(58) Field of Search .................. 514/9, 11, 14, 514/15; 435/68.1, 71.3; 530/317, 323, 327, 328, 333, 336, 338, 343, 345

(56) References Cited

U.S. PATENT DOCUMENTS 4,331,594 A    5/1982   Hamill et al. ............... 530/317

2003/0096948 A1 *  5/2003  Morytko et al. ............ 530/317

FOREIGN PATENT DOCUMENTS

| WO | 0144271 | 6/2001 |
| WO | 0144272 | 6/2001 |
| WO | 0144274 | 6/2001 |

OTHER PUBLICATIONS

DeBono et al. A21978C, A Complex Of New Acidic Peptide Antibiotics . . . The Journal Of Antibiotics. Jun. 1987. vol. 40, No. 6, pp. 761–777.*
U.S. Provisional Application 60/310,313, filed Aug. 6, 2001.*
Drugs Future, 2001, 26(7), pp. 699–700.
Exp Opin. Invest., Drugs (1999)8(8): 1223–1238 F.P. Tally, et al.
Journal of Antibiotics, vol. XLI, No. 8, pp. 1093–1105 Debono, et al (Aug. 1988).

* cited by examiner

*Primary Examiner*—Jeffrey Edwin Russel
(74) *Attorney, Agent, or Firm*—Stanley J. Yavner

(57) ABSTRACT

Novel cyclodepsipeptide intermediates have been prepared from the A21978 complex and used to synthesize new lipodepsipeptide antibiotics. The three intermediates can be readily derivatized to give new families of antibiotics that have potent antibacterial activity against gram positive bacteria.

9 Claims, No Drawings

LIPODEPSIPEPTIDE ANTIBIOTICS AND METHODS OF PREPARATION

FIELD OF THE INVENTION

This invention relates to new lipodepsipeptide antibiotics and methods for preparation of these compounds; and more particularly, a method for preparing novel depsipeptide intermediates from the A21978 antibiotic complex for the purpose of preparing new types of biologically potent lipsipeptides.

BACKGROUND OF THE INVENTION

Daptomycin, which is derived from the A21978 complex, is a lipodepsipeptide antibiotic that is currently undergoing clinical trials (Drugs Future, 2001, 26(7)); F. P. Tally et al., Exp Opin. Invest. Drugs (1999)8(8): 1223–1238) and has shown excellent activity against gram positive bacteria including strains of methicillin-resistant Staphylococcus aureus (MRSA) and vancomycin-resistant enterococci (VRE). Due to resistance of the bacteria, human infections with the MRSA and VRE organisms are very difficult to treat with antibiotics now commercially available. Although daptomycin represents a new structure type for clinically used antibiotics and is active against these infections, its use appears limited by toxicity and a new generation antibiotic in this family with reduced toxicity is needed. A number of derivatives of daptomycin have recently been reported in an effort to accomplish this goal (J. Hill et al., International PCT publication numbers WO 01/44271 A2, WO 01/44272 and WO 01/44274). These and previously reported derivatives are based on building new molecules by adding onto the existing core depsipeptide unit of daptomycin in order to obtain biologically active compounds.

OBJECTS AND SUMMARY OF THE INVENTION

Accordingly, the primary object of the present invention is to provide potent and effective antibiotics for treating gram positive bacteria, without limiting use because of toxicity.

A further object of the present invention is to provide lipodepsipeptide antibiotics, derived from the A21978 complex by selective removal of one to three amino acids of the exocyclic tripeptide side chain of the depsipeptide unit, and then derivatizing the result.

A further and more particular object is to provide nontoxic antibiotics particularly active against gram positive bacterial infections by preparing derivatives of the exocyclic peptide side chain of the depsipeptide unit, after removing one to three amino acids from the side chain.

These and other objects of the present invention are accomplished in an antibiotic which is prepared from three depsipeptide intermediates of the A21978 antibiotic complex. The A21978 complex is obtained by fermentation of *Streptomyces roseosporus*, according to procedures described in U.S. Pat. No. 4,331,594. The ornithine amino group of the A21978 antibiotic complex is then protected by a group, such as 9-fluorenylmethoxycarbonyl (FMOC), or a group from a solid phase support. The product from this reaction is treated with a deacylase enzyme to provide a single protected peptide by removal of the acyl side chain from the components of the complex by procedures described by Debono, et al, in the Journal of Antibiotics, Volume XLI, No. 8, pages 1093–1105. By a sequence of modified Edman degradations or enzymatic reactions, the protected forms of new intermediates are obtained in the form of cyclodepsipeptides. Semi-synthetic antimicrobial lipodepsipeptides are prepared from the cdpeptides. Thus, three different core cdpeptides are elaborated to produce anti-microbial derivatives. The exocyclic tripeptide side chain of the depsipeptide unit is reduced in size by one to three amino acids and then derivatized to produce potent antibiotics.

DETAILED DESCRIPTION OF THE PREFERRED AND ALTERNATIVE EMBODIMENTS

Other objects, features and advantages of the present invention will be provided by the following detailed description of the preferred, but nonetheless illustrative, and alternative, embodiments, as follows:

This invention includes methods for preparing three novel depsipeptide intermediates from the A21978 antibiotic complex that can be used to readily prepare new families of potent lipodepsipeptide antibiotics. The A21978 complex is obtained by fermentation of *Streptomyces roseosporus* according to procedures described in U.S. Pat. No. 4,331,594. In the present invention, the ornithine amino group of the antibiotic complex, is then protected by a group such as 9-fluorenylmethoxycarbonyl (FMOC) or a group from a solid phase support. The product from this reaction is treated with a deacylase enzyme to give a single protected peptide by removal of the acyl side chains from the components of the complex by procedures described by M. Debono (all, as follows):

Reaction Sequence to Obtain Protected Form
of Cdpeptide, Cdpeptide-1, or Cdpeptide-2

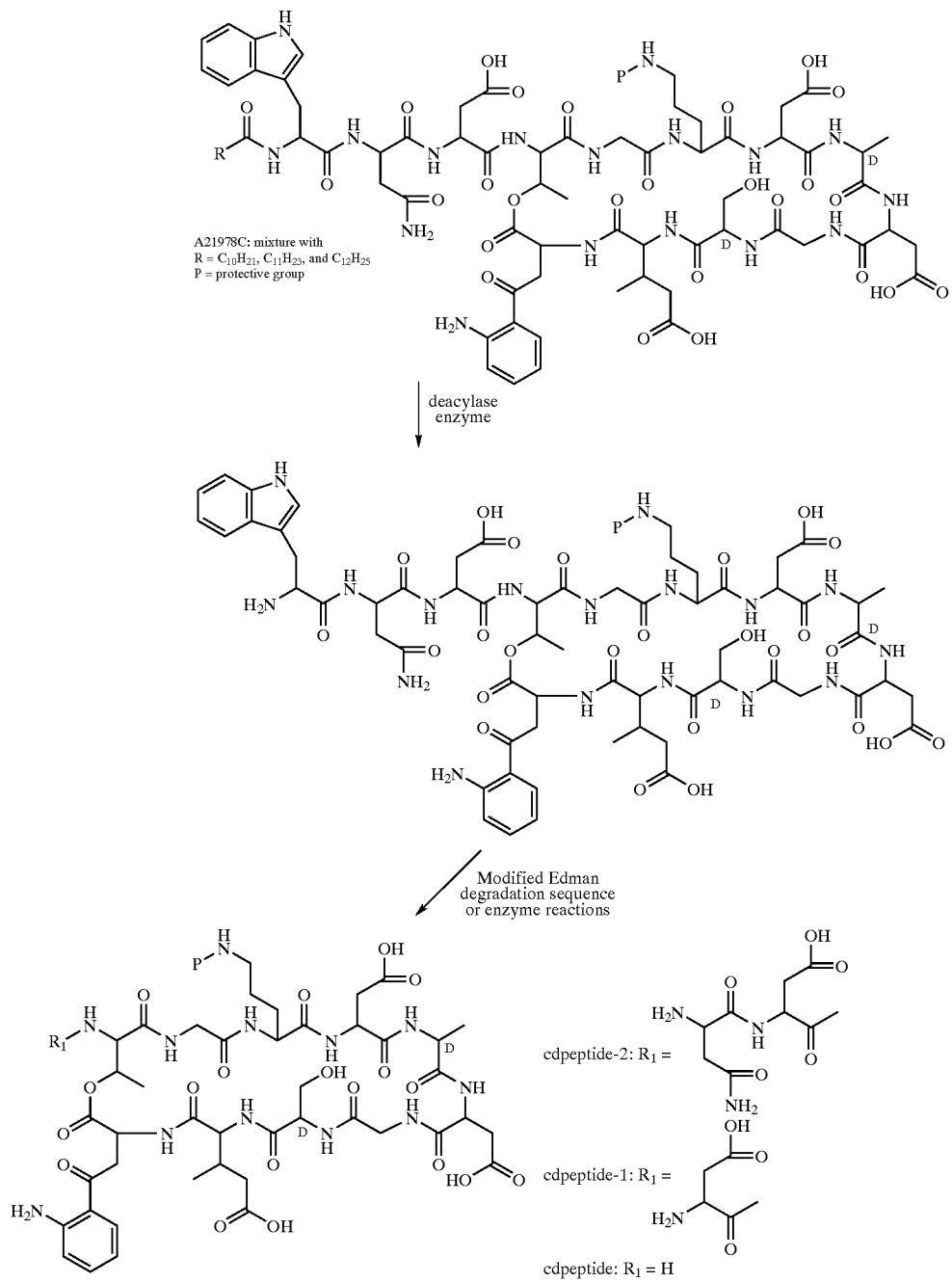

Accordingly, the above scheme shows a sequence of modified Edman degradations or enzymatic reactions to obtain the protected forms of new intermediates designated cdpeptide, cdpeptide-1 and cdpeptide-2, as represented in the following embodiment:

1) H-cdpeptide-P
2) H-(X3)-cdpeptide-P
3) H-(X2)(X3)-cdpeptide-p

Wherein for all three cases H is hydrogen and P is a protective group such as FMOC, CBZ, tBOC, or a solid phase support; X2 is asparaginyl; and X3 is aspartyl.

The present invention also involves semisynthetic antimicrobial lipodepsipeptides and other methods of preparation from the cdpeptides. The three different core cdpeptides are further elaborated to afford antimicrobial derivatives. These derivatives are listed in the following embodiment:

A) A-(X1)(X2)(X3)-cdpeptide
B) A-(X2)(X3)-cdpeptide
C) A-(X3)-cdpeptide

Wherein for Case A) A-(X1)(X2)(X3)-cdpeptide
A=R'—(C=O)—, R'—SO$_2$—, R'—(C=NH)—, R'—(C=S)—, R'—NH—(C=S)—, R'—NH—(C=O)—, R'—O—(C=O)—, R'CH₂—, where R' is alkyl, cycloalkyl, alkenyl, aryl, heteroaryl, or heterocyclic and X1 is an amino acid residue or peptide residue such as L-phenylalanyl, L-kynurenyl, L-β-(1-naphthyl)-alanyl, L-β-(2-naphthyl)-alanyl, L-β-benzothienyl)-alanyl, L-1,2,3,4tetrahydronorharman-3-carbonyl, L-β-(2quinolyl)-alanyl, L-1,2,3,4tetrahydroisoquinoline-3carbonyl, L-tryptophylglycyl, X2 is L-asparginyl or another amino acid residue and X3 is L-aspartyl or another amino acid residue.

For case B) A-(X2)(X3)-cdpeptide
"A" is the same as described for Case A) and X2 is L-asparaginyl or another amino acid residue and X3 is L-aspartyl or another amino acid residue.

For Case C) A-(X3)-cdpeptide
"A" is the same as described in Case A) and X3 is aspartyl or another amino acid residue.

Accordingly, each of these novel cdpeptide intermediates are used to make a new series of potent antibacterial antibiotics by the general procedures described as follows:

Reaction Sequence to obtain Antibiotic Compound 11

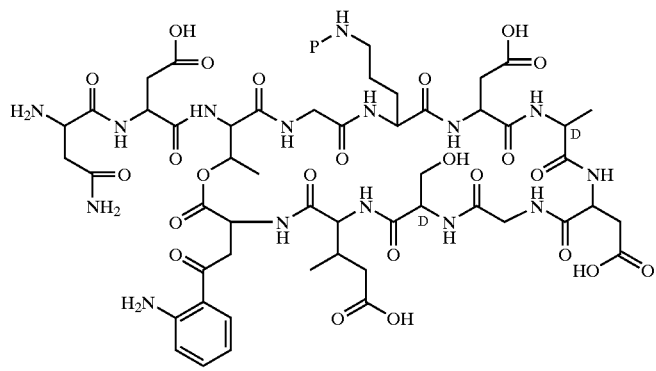

Protected cdpeptide-2

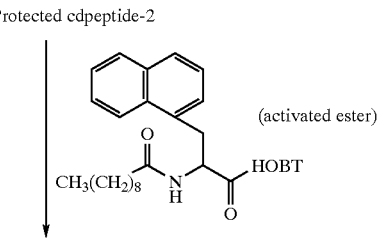

(activated ester)

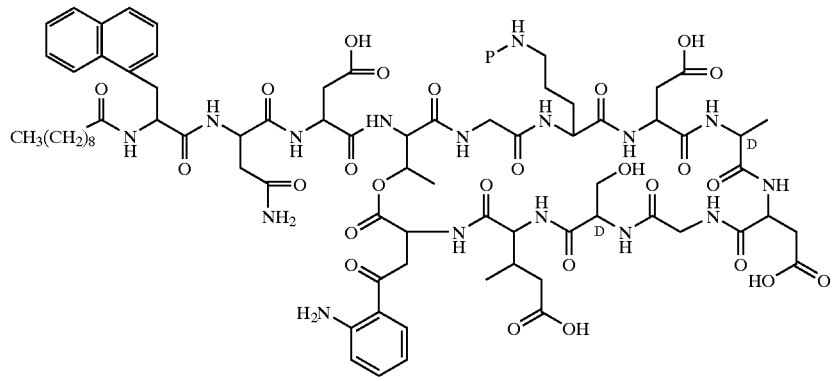

deprotect

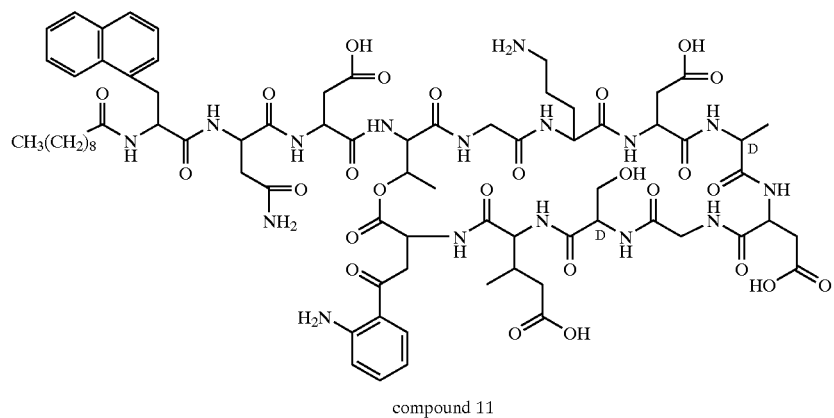
compound 11
Reaction Sequence to obtain Antibiotic Compound 1
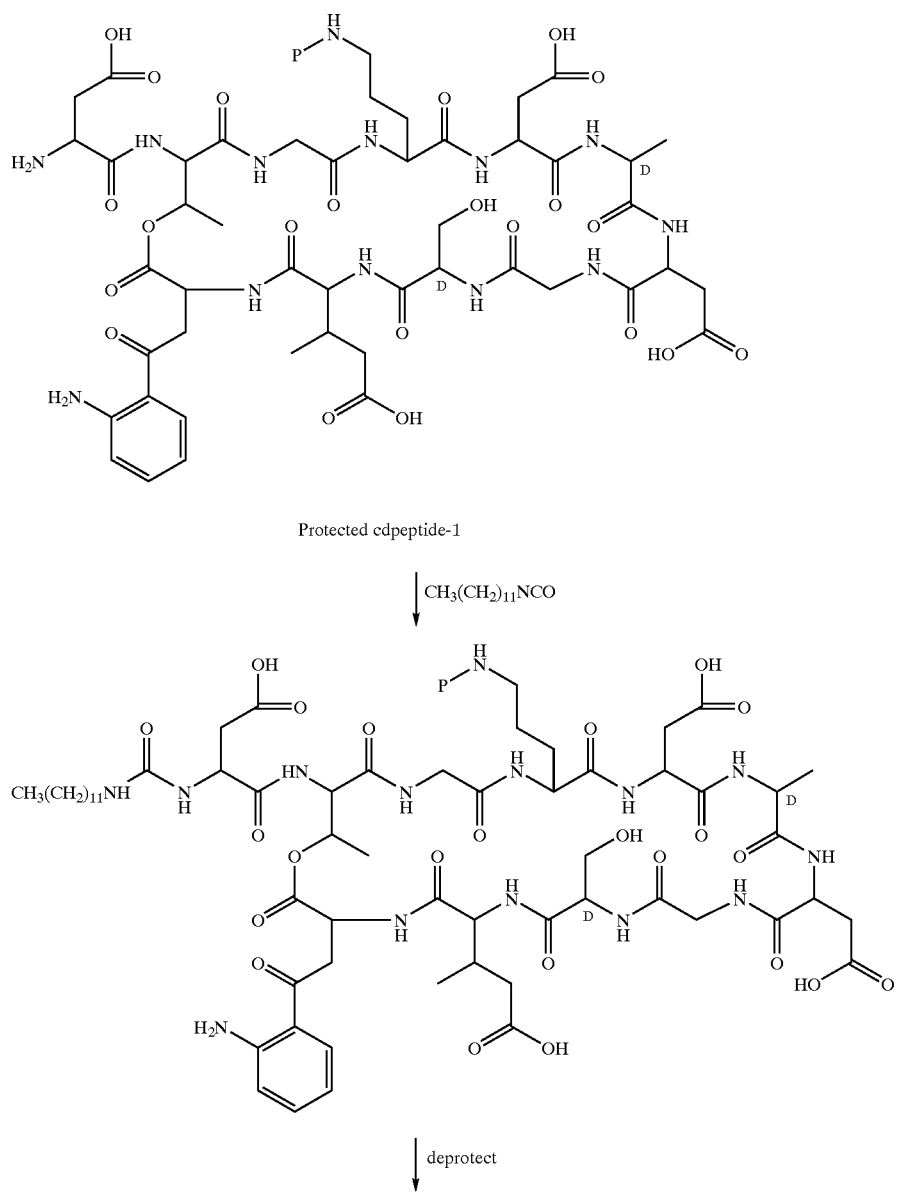
Protected cdpeptide-1
| CH₃(CH₂)₁₁NCO
↓ deprotect

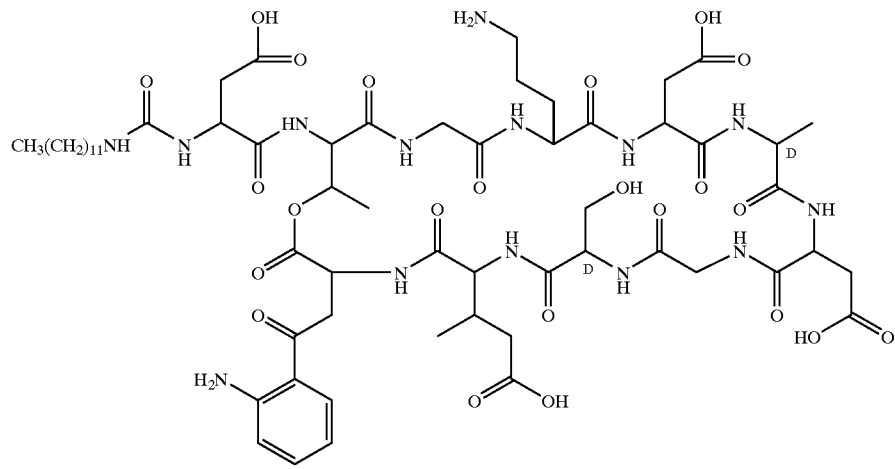

compound 1

Amino acids derivative are synthesized for a number of the coupling reactions and are summarized in the following Table 1:

TABLE 1

Amino Acid Derivatives Synthesized for Coupling Reactions

| Name | MF | FABMS |
|---|---|---|
| N-Decanoyl-L-phenylalanine | $C_{19}H_{29}NO_3$ | 320(M + H)$^+$, 342(M + Na)$^+$ |
| N-Decanesulfonyl-L-phenylalanine | $C_{19}H_{31}NO_4S$ | 370(M + H)$^+$, 392(M + Na)$^+$ |
| N-Decanoyl-L-kynurenine | $C_{20}H_{30}N_2O_4$ | 363(M + H)$^+$ |
| N-Decanoyl-L-β-(1-naphthyl)-alanine | $C_{23}H_{31}NO_3$ | 370(M + H)$^+$, 392(M + Na)$^+$ |
| N-Decanoyl-L-β-(2-naphthyl)-alanine | $C_{23}H_{31}NO_3$ | 370(M + H)$^+$, 392(M + Na)$^+$ |
| N-Decanoyl-L-β-(3-benzothienyl)-alanine | $C_{21}H_{29}NO_3S$ | 376(M + H)$^+$, 398(M + Na)$^+$ |
| N-Decanoyl-L-1,2,3,4-tetrahydronorharman-3-carboxylic acid | $C_{22}H_{30}N_2O_3$ | 370(M)$^+$, 393(M + Na)$^+$ |
| N-Decanoyl-L-β-(2-quinolyl)-alanine | $C_{22}H_{30}N_2O_3$ | 371(M + H)$^+$ |
| N-Decanoyl-L-1,2,3,4-tetrahydroisoquinoline-3-carboxylic acid | $C_{20}H_{29}NO_3$ | 332(M +H)$^+$, 354(M + Na)$^+$ |
| N-Dodecylcarbamoyl-L-β-(2-naphthyl)-alanine | $C_{26}H_{38}N_2O_3$ | 427(M + H)$^+$, 449(M + Na)$^+$ |

Abbreviations for Table 2: L-β-(3-benzothienyl)-alanine (L-Bthio); L-1,2,3,4-tetrahydronorharman-3-carboxylic acid (L-Harm); L-β-(1-naphthyl)-alanine (L-1-Nath); L-β-(2-naphthyl)-alanine (L-2-Naph).

The acyl amino acids are then coupled to the protected intermediate cdpeptide, and deprotected to give the new antibiotic as shown in the foregoing reaction sequence to obtain Antibiotic Compound 11, and represented by compounds 5, 6, 9–14, 16, 17, as listed in the headings for the various Examples to be set forth hereinafter.

The protected intermediate cdpeptides are also derivatized directly and the products deprotected to give a series of antibiotics as shown above in the reaction sequence to obtain Anti-biotic Compound 1, and also represented by compounds 2, 3, 4 and 15, as set forth in the headings for the various Examples to be provided hereinafter. The biological activities of some of the new antibiotics prepared pursuant to this invention are given in the following Table 2:

TABLE 2

Minimum Inhibitory Concentations (MIC) for New Lipopeptide Antibiotics

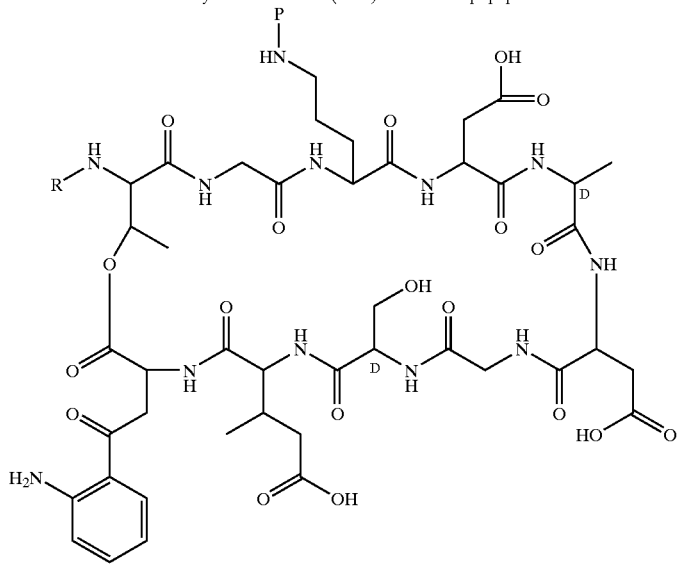

Cyclodepsipeptide(cdpeptide), R & X = H
R = lipid - amino acd side chain
P = protective group or hydrogen

| compound name | structure** | MIC vs. *S. aureus** | |
|---|---|---|---|
| | | wo Ca++ | w Ca++ |
| daptomycin | CH₃(CH₂)₈CO-Trp-Asn-Asp-cdpeptide | 2.5 | 0.16 |
| tBOC daptomycin | CH₃(CH₂)₈CO-Trp-Asn-Asp-tBOC-cdpeptide | >2.5 | 0.6 |
| 1 | CH₃(CH₂)₁₁NHCO-Asp-cdpeptide | >20 | 10.0 |
| 2 | CH₃(CH₂)₁₁NHCO-Asn-Asp-FMOC-cdpeptide | >20 | 5.0 |
| 3 | CH₃(CH₂)₁₁NHCO-Asn-Asp-cdpeptide | >20 | 2.5 |
| 4 | CH₃(CH₂)₁₁CO-Asn-Asp-cdpeptide | >20 | >10 |
| 5 | CH₃(CH₂)₈CO-L-Phe-Asn-Asp-cdpeptide | >5.0 | 0.6 |
| 6 | CH₃(CH₂)₈CO-D-Phe-Asn-Asp-cdpeptide | >20 | 5.0 |
| 7 | CH₃(CH₂)₉SO₂-L-Phe-Asn-Asp-cdpeptide | >20 | 2.5 |
| 8 | CH₃(CH₂)₉SO₂-L-Phe-Asn-Asp-FMOC-cdpeptide | >20 | 5.0 |
| 9 | CH₃(CH₂)₈CO-L-Kyn-Asn-Asp-cdpeptide | 5.0 | 0.6 |
| 10 | CH₃(CH₂)₈CO-D-Kyn-Asn-Asp-cdpeptide | >20 | 20 |
| 11 | CH₃(CH₂)₈CO-L-1-Naph-Asn-Asp-cdpeptide | 2.5 | 0.16 |
| 12 | CH₃(CH₂)₈CO-L-Bthio-Asn-Asp-cdpeptide | 2.5 | 0.16 |
| 13 | CH₃(CH₂)₈CO-L-Harm-Asn-Asp-cdpeptide | >10 | 5.0 |
| 14 | CH₃(CH₂)₈CO-D-Harm-Asn-Asp-cdpeptide | >10 | >10 |
| 15 | CH₃(CH₂)₁₅NHCO-Asn-Asp-cdpeptide | 2.5 | 2.5 |
| 16 | CH₃(CH₂)₁₁NHCO-L-2-Naph-Asn-Asp-cdpeptide | 0.32 | 0.16 |
| 17 | CH₃(CH₂)₈CO-L-2-Naph-Asn-Asp-cdpeptide | 2.5 | 0.08 |

*MIC values were determined by serial twofold broth dilution method using *Staphlococcus aureus* strain Smith as assay organism which was grown in Mueller Hinton broth without and with 4 mmolar CaCl₂.
**Abbreviations: see Table 1.

Another variation or series of new antibiotics, according to the present invention, is represented by the sulfonyl derivatives (Table 2-Compounds 7 and 8, and Example 2 hereinafter). The lipid side chains from these compounds are attached to the cdpeptides by a sulfonyl group. Other linkers such as carbamoyl are possible (Table 2, compounds 1, 3, 15 and 16) and give compounds with good antibacterial activity.

The effect of stereochemistry of amino acids in the side chains is illustrated by compounds 9 and 10 of Table 2. Compound 9, which presumably has L-kynurenine in the side chain is approximately thirty times more active than the corresponding compound 10 with a presumed D-kynurenine configuration.

The amino acid derivatives listed in the foregoing Table 1 are all new compounds except N-decanoyl-L-phenylalanine. All of the acyl compounds were prepared by procedures similar to those described in Example 1 hereinafter for the preparation of the N-decanoyl-L-β-(2-naphthyl)-alanine. This involves preparation of an activated ester of the decanoic acid or other fatty acids and reacting the resulting activated esters with the amino acids. For the compounds given in the foregoing Table 1, all of the amino acids are commercially available. The N-dodecylcarbamoyl-L-β-(2-naphthyl)-alanine is an N-alkyl urea type derivative of an amino acid and is prepared by reacting dodecylisocyanate with the amino acid as described in Example 3 hereinafter. These products and the others listed in the foregoing Table 1 were analyzed for purity by TLC and HPLC and characterized by fast atom bombardment mass spectrometry (FABMS).

As referred to above, the following Examples are provided in order to enable a complete understanding of the method of preparation, the depsipeptide intermediates for the preparation of antibiotics, and the products obtained from the method.

EXAMPLES

1) N-Decanoyl-L-β-(2-naphthyl)-alanine

To a stirred solution of L-β-(2-naphthyl)-alanine (100 mg, 0.464 mmol) in 0.50 ml 1.0N sodium hydroxide, 0.50 ml water, and 1.0 ml tetrahydrofuran was added a solution of decanoic acid 1-hydroxybenzotriazole ester (134 mg, 0.464 mmol) in 1.0 ml of tetrahydrofuran in several portions. The mixture was stirred at room temperature overnight, then diluted with water (10 ml) and extracted with ethyl acetate (15 ml). The ethyl acetate extract was washed with water and then dried over magnesium sulfate. Evaporation of the ethyl acetate gave an oil which was triturated to a solid with hexane to afford 85 mg of the desired product (see Table 1). Thin layer chromatography (TLC) on Whatman® K6F silica gel 60 A, 250 μm plates developed with chloroform: methanol: 3% ammonium hydroxide (5:5:1) gave Rf 0.80. FABMS m/z 370(M+H)$^+$, 392(M+Na)$^+$, Calculated for $C_{23}H_{32}NO_3$, 370.24; $C_{23}H_{31}NO_3Na$, 392.22.

2) N-Decanesulfonyl-L-phenylalanine

A solution of decanesulfonyl chloride (0.8571 g, 3.56 mmol) in ether (7.5 ml) was added to a solution of L-phenylalanine (0.7441 g, 4.40 mmol) in 10 ml of 1.0 N sodium hydroxide and stirred at room temperature overnight. The reaction mixture was extracted with ethyl acetate and the aqueous phase was separated and acidified to pH 1 with 6 N hydrochloric acid. The resulting precipitate was extracted into ethyl acetate and the extract was washed with water and dried with magnesium sulfate. Evaporation of the ethyl acetate gave an oil which crystallized (see Table 1). Yield 0.245 g; FABMS m/z 370(M+H)$^+$, 392(M+Na)$^+$, Calculated for $C_{19}H_{32}NO_4S$, 370.20; $C_{19}H_{31}NO_4SNa$, 392.19.

3) N-Dodecylcarbamoyl-L-β-(2-naphthyl)-alanine

To a stirred mixture of L-β-(2-naphthyl)-alanine (0.1093 g, 0.5026 mmol) and diisopropylethylamine (0.16 ml, 0.5751 mmol) in 2 ml of THF and 2 ml of water was added dodecylisocyanate (0.123 ml, 0.5076 mmol). Solution was complete in about 15–20 min and stirring was continued for 1.5 hrs. Water (5 ml) was added and the solution was acidified to pH 2 with 6 N hydrochloric acid. The mixture was extracted with ethyl acetate which was washed with water and brine then dried over magnesium sulfate. Evaporation of the ethyl acetate gave a white solid, 0.1948 g, TLC (see Example 1) zone at Rf 0.60; FABMS m/z 427(M+H)$^+$, 449(M+Na)$^+$, calc. for $C_{26}H_{39}N_2O_3$, 427.30, $C_{26}H_{38}N_2O_3Na$, 449.28.

4) FMOC-Cyclodepsipeptide-2

Twenty milligrams of deacylated FMOC-A21978 complex was dissolved in 1.0 mL of potassium borate in 50% methanol (0.25 M in borate, aqueous dilution pH 8.8). Phenylisothiocyanate (PITC) (0.010 mL) was added, the reaction mixture flushed with argon, placed in an ultrasonic bath to disperse the PITC, then stirred at room temperature (RT). The progress of the reaction was monitored by high performance liquid chromatography (HPLC). After 120 min the reaction was about 95% complete. The reaction mixture was diluted with 2 mL of ammonium phosphate buffer (0.4M in phosphate, pH 7.2) and 0.5 mL acetonitrile ($CH_3CN$) then 0.45 micron membrane filtered. The phenylthiocarbamyl PTC derivative was isolated from the reaction mixture filtrate by low resolution reverse phase chromatograhpy on a 0.5 g styrene-divinylbenzene resin cartridge (Supelco ENVI™-Chrom P). The sample solution was applied to the cartridge which was then rinsed with about 6 mL of 25% $CH_3CN$, 0.10 M in pH7.2 ammonium phosphate buffer. The product was eluted with 33% $CH_3CN$ 0.07 M pH 7.2 buffer; this eluate was diluted with an equal volume of distilled water. Desalting of this solution was done by adsorption of the PTC product onto an ENVI-Chrom-P 0.5 g resin cartridge; the cartridge was rinsed with 6 mL of 6% $CH_3CN$ (salt-free) and the product was stripped from the resin with 6 mL of 67% $CH_3CN$. $CH_3CN$ was removed under vacuum at 30° C. and the aqueous solution was freeze dried. Yield: 18.7 mg of a light yellow solid; 89% by HPLC (215 nm area %).

To remove the PTC-Trp residue, the solid product (18.7 mg) was dissolved in 1 mL of trifluoroacetic acid (TFA), the container flushed with argon then sealed; the solution was heated at 50° C. for 20 min. TFA was removed with a stream of dry nitrogen and the residue was dissolved in 5 mL of 0.4M pH 7.2 ammonium phosphate buffer; solution pH was about 7. The product was isolated by adsorption onto an ENVI-Chrom-P 0.5 g resin cartridge followed by rinsing with 4 mL of 4% $CH_3CN$ then elution with 6 mL of 50% $CH_3CN$. $CH_3CN$ was removed under vacuum and the product solution was freeze dried. Yield: 16.3 mg of a light yellow solid, purity about 40% by HPLC (215 nm area %). This product was further purified on an ENVI-Chrom-P 0.5 g resin cartridge. The solid (15.7 mg) was dissolved in 4 mL of 20% $CH_3CN$, 0.08M in ammonium phosphate pH 7.2 buffer, and applied to the cartridge which was eluted with 25% $CH_3CN$, 0.10 M in pH 7.2 buffer. Product-containing fractions (as determined by analytical HPLC) were pooled, desalted and freeze dried as described above. Yield: 10.3 mg of a pale yellow solid, 85% by HPLC; $C_{66}H_{83}N_{15}O_{26}$; FABMS m/z 1502 (M+H)$^+$, 1524 (M+Na)$^+$; calc. for $C_{66}H_{84}N_{15}O_{26}$, 1502.57, $C_{66}H_{83}N_{15}O_{26}$, Na, 1524.55.

5) FMOC-Cyclodepsipeptide-1

FMOC-cyclodepsipeptide-2 (10.3 mg) was dissolved in 0.60 mL of pH 8.8 potassium borate in 50% methanol and reacted with 0.010 mL of PITC as in Example 4, 80 min at RT then 25 min at 50° C. The reaction mixture was diluted with 2 mL 0.4 M pH 7.2 buffer and 0.2 mL $CH_3CN$, membrane filtered, then applied to an ENVI-Chrom-P 0.5 g resin cartridge. The cartridge was eluted with stepwise increasing concentrations of $CH_3CN$ buffered with pH 7.2 ammonium phosphate; the PTC product was eluted with 25% $CH_3CN$, 0.10 M in pH 7.2 buffer. Product-containing fractions were desalted and freeze dried as in Example 4. Yield: 8.6 mg of a pale yellow solid, 82% by HPLC (215 nm area %).

The PTC-Asn residue was cleaved by treatment with TFA and the product was isolated using an ENVI-Chrom-P 0.5 g resin cartridge as in Example 4; product was eluted with about 22% $CH_3CN$, 0.04 M in pH 7.2 buffer. The product-containing fractions were desalted and freeze dried as in Example 4. Yield: 5.1 mg of a pale yellow solid, 85% by HPLC (215 nm area %); $C_{62}H_{77}N_{13}O_{24}$; FABMS m/z 1389 (M+H)$^+$, 1411 (M+Na)$^+$; calc. for $C_{62}H_{78}N_{13}O_{24}$, 1388.53; $C_{62}H_{77}N_{13}O_{24}Na$, 1410.51.

6) FMOC-Cyclodepsipeptide

Modified Edman Degradation Method

FMOC-cyclodepsipeptide-1 (9.8 mg) was dissolved in 0.60 mL of pH 8.8 potassium borate in 50% methanol and reacted with 0.010 mL of PITC as in Example 4, 80 min at RT then 25 min at 50° C. The reaction mixture was diluted with 2 ML 0.4 M pH 7.2 buffer and 0.2 mL $CH_3CN$, membrane filtered, then applied to an ENVI-Chrom-P 0.5 g resin cartridge. The cartridge was eluted with stepwise increasing concentrations of $CH_3CN$ buffered with pH 7.2 ammonium phosphate; the PTC product was eluted with 28% $CH_3CN$, 0.10 M in pH 7.2 buffer. Product-containing fractions were desalted and freeze dried as in Example 4. Yield: 7.6 mg of a pale yellow solid, 86% by HPLC (215 nm area %).

The PTC-Asp residue was cleaved by treatment with TFA and the product was isolated using an ENVI-Chrom-P 0.5 g resin cartridge as in Example 4; product was eluted with about 25% $CH_3CN$, 0.04 M in pH 7.2 buffer. The product-containing fractions were desalted and freeze dried as in Example 4. Yield: 3.6 mg of a pale yellow solid, 83% by HPLC (215 nm area %); $C_{58}H_{72}N_{12}O_{21}$.

Enzymatic Method

FMOC-cyclodepsipeptide-2 (2.7 mg) was dissolved in 1.4 mL of 0.02M sodium citrate buffer (pH 6.4) and 0.006M in 2-mercaptoethylamine(MEA) hydrochloride. The enzyme solution was prepared by dissolving 10 units (0.9 mg) of cathepsin C (dipeptidyl aminopeptidase)(EC 3.4.14.1) in 1.0 mL of the citrate-MEA buffer. Enzyme solution (0.25 mL) was added to the peptide solution which was incubated at about 37° C. for about 24 hours. HPLC analysis indicated about 75% conversion to FMOC-cyclodepsipeptide with no FMOC-cyclodepsipeptide-1. The incubated solution was diluted with 11.0 mL 0.4M pH7.2 ammonium phosphate buffer, 3.0 mL distilled water and 0.5 mL $CH_3CN$. The product was isolated on an ENVI-Chrom-P 0.5 g resin cartridge; product was eluted with 25% $CH_3CN$, 0.05M in pH7.2 buffer. After HPLC evaluation, product-containing fractions (accounting for about 72% of the total product) were pooled, desalted and freeze dried as in Example 4. Yield: 1.0 mg of a pale yellow solid, 87% by HPLC (215 nm area %); $C_{58}H_{72}N_{12}O_{21}$; FABMS m/z 1273 $(M+H)^+$, 1295 $(M+Na)^+$, 1311 $(M+K)^+$; calc. for $C_{58}H_{73}N_{12}O_{21}$, 1273.50; $C_{58}H_{72}N_{12}O_{21}Na$, 1295.48, $C_{58}H_{72}N_{12}O_{21}K$, 1311.46.

7) N-Dodecylcarbamoyl-cyclodepsipeptide-1 (Compound 1)

FMOC-cyclodepsipeptide-1 (5.0 mg) was dissolved in 0.20 mL of 0.25 M potassium borate in 50% methanol (aqueous pH 8.8) and 0.20 mL of methanol; 0.004 mL of dodecylisocyanate was added, dispersed by ultrasonication, and the mixture stirred at room temperature. The reaction was monitored by HPLC. After 45 min the reaction mix was diluted with 2 mL of 0.4 M ammonium phosphate pH 7.2 buffer and 0.2 mL methanol, ultrasonicated, and 0.45 micron membrane filtered. The product was isolated by low resolution reverse phase chromatography on an ENVI-Chrom-P 0.5 g resin cartridge. The filtrate of the reaction mixture was applied to the cartridge which was eluted with stepwise increasing concentrations of $CH_3CN$, about 0.08 M in pH 7.2 buffer; product was eluted with 40% $CH_3CN$. Product-containing fractions (as determined by HPLC) were pooled, diluted with an equal volume of distilled water and applied to a fresh ENVI-Chrom-P 0.5 g resin cartridge for desalting. The cartridge was rinsed with 4 mL of 4% $CH_3CN$ (salt-free) and product was eluted with 6 mL of 67% $CH_3CN$. $CH_3CN$ was removed under vacuum at 30° C. and the remaining aqueous solution was freeze dried. Yield: 4.6 mg of a pale yellow solid, 90% by HPLC (215 nm area %); $C_{75}H_{102}N_{14}O_{25}$.

The FMOC-protected product (4.6 mg) was dissolved in 0.50 mL of dimethylsulfoxide/methanol (DMSO/MeOM) (2/1), flushed with argon, 0.010 mL of piperidine added, flushed with argon and the container sealed. The reaction mixture was aged for 75 min at RT then diluted with 2 mL of 0.4M pH 7.2 buffer and 4 mL of 8% AcN, then membrane filtered. The product was isolated from the filtrate by adsorption onto an ENVI-Chrom-P 0.5 g resin cartridge. The cartridge was rinsed with 4 mL of 4% $CH_3CN$ to remove buffer salts and reaction solvents, then the product was eluted with 6 mL of 50% $CH_3CN$. $CH_3CN$ was removed under vacuum and the solution was freeze dried. Yield: 3.8 mg of a pale yellow solid, 89% by HPLC (215 nm area %); $C_{62}H_{77}N_{13}O_{24}$; FABMS m/z 1377.5 $(M+H)^+$, 1399.5 $(+Na)^+$, 1415.5 $(M+K)^+$.calc. for $C_{62}H_{78}N_{13}O_{24}$, 1377.65; $C_{62}H_{77}N_{13}O_{24}Na$, 1399.64; $C_{62}H_{77}N_{13}O_{24}K$; 1415.61.

8) N-Dodecylcarbamoyl-cyclodepsipeptide-2 (Compound 3)

FMOC-cyclodepsipeptide-2 (5.2 mg) was dissolved and reacted with 0.004 mL of dodecylisocyanate as in Example 7. After 50 min the reaction mixture was diluted with 2 mL of 0.4 M ammonium phosphate pH 7.2 buffer, ultrasonicated, and membrane filtered. The FMOC-product was isolated and desalted as described in Example 7. Yield: 3.4 mg of a pale yellow solid, 90% by HPLC (215 nm area %); $C_{79}H_{108}N_{16}O_{27}$.

The FMOC-protected product (3.4 mg) was deblocked, isolated, desalted and freeze dried as in Example 7. Yield: 2.7 mg of a pale yellow solid, 86% by HPLC (215 nm area %); $C_{64}H_{98}N_{16}O_{25}$; FABMS m/z 1491 $(M+H)^+$, 1513 $(M+Na)^+$, 1529 $(M+K)^+$.calc. for $C_{63}H_{99}N_{16}O_{25}$, 1491.70; $C_{64}H_{98}N_{16}O_{25}Na$, 1513.68; $C_{64}H_{98}N_{16}O_{25}K$, 1529.65.

9) N-Decanoyl-L/D-phenylalanyl-cyclodepsipeptide-2 (Compounds 5P, 6P: 5, 6)

A mixture of N-decanoyl-L-phenylalanine (0.128 g, 0.40 mmol), 1-hydroxybenzotriazole (HOBT, 0.061 g, 0.40 mmol) and dicyclohexylcarbodiimide (DCC, 0.082 g, 0.40 mmol) was dissolved in 0.86 mL of dimethylformamide (DMF) and stirred at RT for about 45 min (in situ activated ester solution). FMOC-cyclodepsipeptide-2 (8.8 mg, 0.006 mmol) was dissolved in 0.20 mL of DMF; three 0.015 mL aliquots of the activated ester solution were added over time and the reaction was monitored by HPLC. After 140 min at RT the reaction mixture was diluted with 1.0 mL of 0.4 M ammonium phosphate pH 7.2 buffer, 1.0 mL distilled water and 0.8 mL MeOH, ultrasonicated and membrane filtered. Product was isolated by low resolution reverse phase chromatography on an ENVI-Chrom-P 0.5 g resin cartridge. The product was adsorbed onto the cartridge which was then eluted with stepwise increasing concentrations of $CH_3CN$ in pH 7.2 ammonium phosphate buffer; product was eluted using 33% $CH_3CN$, 0.07 M in pH 7.2 buffer. The product-containing fractions (determined by HPLC) were pooled, desalted and freeze dried as is Example 7. Yield: 6.6 mg of a pale yellow solid which by HPLC contained two partially resolved components in an approximate 3/2 ratio.

The FMOC-protected products (6.6 mg) were deblocked as in Example 7. After 60 min at RT the reaction mixture was diluted with 2.0 mL of 0.4 M pH 7.2 buffer, 2.0 mL distilled water and 1.0 mL $CH_3CN$, aged about 20 min at RT then membrane filtered. The products were purified by preparative HPLC on a Delta-Pak™ C18 column (Waters Corp., 25×210 mm, 15 micron particle) isocratically eluted at RT with 34% $CH_3CN$, 0.016 M in ammonium phosphate buffer, pH 7.2. Fractions were evaluated by analytical HPLC; appropriate fractions were pooled, $CH_3CN$ removed under vacuum at 30° C., desalted and freeze dried in fashion similar to Example 7. The desired compound was obtained as two diastereomers and the presumed phenylalanine configuration in each diastereomer is indicated below.

Yields: L-isomer: 2.9 mg of a pale yellow solid, 100% by HPLC (215 nm area %); $C_{70}H_{100}N_{16}O_{26}$; FABMS m/z 1581 $(M+H)^+$, 1603 $(M+Na)^+$, 1619 $(M+K)^+$; calc. for $C_{70}H_{101}N_{16}O_{26}$, 1581.71, $C_{70}H_{100}N_{16}O_{26}$ Na, 1603.69, $C_{70}H_{100}N_{16}O_{26}K$, 1619.66. D-isomer: 1.7 mg of a pale yellow solid, 100% by HPLC (215 nm area %); $C_{70}H_{100}N_{16}O_{26}$; FABMS m/z 1581 (N+H)$^+$, 1603 (M+Na)$^+$, 1619 (M+K)$^+$.

10) N-Decanesulfonyl-L-phenylalanyl-cyclodepsipeptide-2 (Compounds 7 and 8)

A mixture of N-decanesulfonyl-L-phenylalanine (0.074 g, 0.20 mmol), diisopropylethylamine (DIEA) (0.035 mL, 0.20 mmol) and O-[(ethoxycarbonyl) cyanomethylamino]-N,N, N'N'tetramethyluronium tetrafluoroborate (TOTU) (0.065 g, 0.20 mmol) was dissolved in 0.88 mL DMF and stirred at RT for about 60 min (in situ activated reagent solution). FMOC-cyclodepsipeptide-2 (8.5 mg, 0.006 mmol) was dissolved in 0.20 mL of DMF; three 0.060 mL aliquots of the activated reagent solution were added to the stirred reaction at RT over 140 minutes. The reaction was monitored by HPLC. The reaction mixture was diluted with 1.0 mL of 0.4 M ammonium phosphate pH 7.2 buffer, 1.0 mL distilled water, and 0.8 mL MeOH, ultrasonicated and membrane filtered. The product was purified by preparative HPLC on a Delta-Pak C18 column (Waters Corp., 25×210 mm, 15 micron particle) using stepwise gradient elution at RT. The product was eluted with about 46% CH$_3$CN, 0.01 M in ammonium phosphate buffer, pH 7.2. Fractions were evaluated by HPLC; appropriate fractions were pooled and CH$_3$CN removed under vacuum at 30° C. The aqueous solution was applied to an ENVI-Chrom-P 0.5 g resin cartridge which was then rinsed with 4 mL of distilled water. The desalted product was eluted with 6 mL of 67% CH$_3$CN; the CH$_3$CN was removed under vacuum at 30° C. and the aqueous solution was freeze dried. Yield: 4.5 mg of a pale yellow solid, 100% by HPLC (215 nm area %); $C_{85}H_{112}N_{16}O_{29}S$.

The FMOC-protected product (4.0 mg) was deblocked as in Example 9. After 60 min at RT the reaction mixture was diluted with 2.0 mL of 0.4M pH 7.2 buffer, 2.0 mL distilled water and 1.0 mL CH$_3$CN. The product was isolated by adsorption onto an ENVI-Chrom-P 0.5 g cartridge which was rinsed with 4 mL of distilled water then the product was eluted with 6 mL of 67% CH$_3$CN. The CH$_3$CN was removed under vacuum and the solution was freeze dried. Yield: 3.6 mg of a pale yellow solid, 100% by HPLC (215 nm area %); $C_{70}H_{102}N_{16}O_{27}S$; FABMS m/z 1632 (M+H)$^+$, 1654 (M+Na)$^+$, 1670 (M+K)$^+$; calc. for $C_{70}H_{103}N_{16}O_{27}S$, 1631.69; $C_{70}H_{102}N_{16}O_{27}SNa$, 1653.67; $C_{70}H_{102}N_{16}O_{27}SK$, MW 1669.65.

11) N-Decanoyl-L/D-kynurenyl cyclodepsipeptide-2 (Compounds 9P. 10P: 9. 10)

A mixture of N-decanoyl-L-kynurenine (0.049 g, 0.136 mmol), DIEA (0.024 mL, 0.136 mmol) and TOTU (0.045 g, 0.136 mmol) was dissolved in 1.2 mL of DMF and stirred at RT for about 60 min (in situ activated reagent solution). FMOC-cyclodepsipeptide-2 (10.6 mg, 0.007 mmol) was dissolved in 0.20 mL of DMF; multiple aliquots of the activated reagent solution were added over time, the reaction stirred at RT and monitored by HPLC. After about 5 hrs and about 0.6 mL of added activated reagent, the reaction mixture was diluted with 2.0 mL of 0.4 M ammonium phosphate pH 7.2 buffer, 2.0 mL distilled water, 1.0 mL CH$_3$CN and 0.8 mL MeOH, then ultrasonicated. Product was isolated by low resolution reverse phase chromatography on an ENVI-Chrom-P 0.5 g resin cartridge as in Example 9. The product-containing fractions (determined by HPLC) were pooled, desalted and freeze dried as in Example 10. Yield: 10.9 mg of a tan solid which by HPLC contained two partially resolved components in an approximate 3/2 ratio.

The FMOC-protected products (9.2 mg) were deblocked as in Example 9. After 45 min at RT the reaction mixture was diluted with 2.0 mL of 0.4 M pH 7.2 buffer, 3.0 mL distilled water and 1.0 mL CH$_3$CN. The products were isolated on an ENVI-Chrom-P 0.5 g cartridge as in Example 9; products were eluted with about 28% CH$_3$CN, 0.04M in pH 7.2 ammonium phosphate buffer. Fractions were pooled, desalted and freeze dried as in Example 10. Yield: 5.2 mg of a light tan solid, still containing a mix of the two products.

The products were separated by preparative HPLC on a Delta-Pak C 18 column (Waters Corp., 25×210 mm, 15 micron particle) using a short stepwise gradient elution at RT. The products were eluted with about 33% CH$_3$CN, 0.016 M in ammonium phosphate buffer, pH 7.2. Fractions were evaluated by HPLC. Appropriate fractions were pooled, CH$_3$CN removed under vacuum at 30° C., desalted and freeze dried as in Example 10. The desired compound was obtained as two diastereomers and the presumed kynurenine configuration in each diastereomer is indicated below.

Yields: L-isomer: 2.5 mg of a pale yellow solid, 96% by HPLC (215 nm area %); $C_{71}H_{101}N_{17}O_{27}$, FABMS m/z 1625 (M+H)$^+$, 1647 (M+Na)$^+$, 1663 (M+K)$^+$; Calc. for $C_{71}H_{102}N_{17}O_{27}$, 1624.71; $C_{71}H_{101}N_{17}O_{27}Na$, 1646.70; $C_{71}H_{101}N_{17}O_{27}K$, 1662.67. D-Isomer: 1.7 mg of a pale yellow solid, 95% by HPLC (215 nm area %); $C_{71}H_{101}N_{17}O_{27}$,; FABMS m/z 1625 (M+H)$^+$, 1647 (M+Na)$^+$, 1663 (M+K)$^+$.

12) N-Decanoyl-L-β-(1-naphthyl)alanyl-cyclodepsipeptide-2 (Compound 11)

A mixture of N-decanoyl-L-β-(1-naphthyl)-alanine (0.063 g, 0.171 mmol), HOBT (0.026 g, 0.171 mmol) and DCC (0.035 g, 0.171 mmol) was dissolved in 0.45 mL of DMF and stirred at RT for about 45 min (in situ activated ester solution). FMOC-cyclodepsipeptide-2 (7.2 mg, 0.005 mmol) was dissolved in 0.20 mL of DMF; three aliquots (0.050 mL total) of the activated ester were added over time and the reaction was monitored by HPLC. After 105 min at RT the reaction mixture was quenched and product was isolated as in Example 9. The product-containing fractions (determined by HPLC) were pooled, desalted and freeze dried as is Example 10. Yield: 4.8 mg of a pale yellow solid, 86% by HPLC (264 nm area %).

The FMOC-protected product (4.8 mg) was deblocked as in Example 9. After 45 min at RT the reaction mixture was diluted with 2.0 mL of 0.4 M pH 7.2 buffer, 3.0 mL distilled water and 1.0 mL CH$_3$CN. The product was isolated on an ENVI-Chrom-P 0.5 g cartridge as in Example 9; the product was eluted with about 29% CH$_3$CN, 0.06 M in pH 7.2 ammonium phosphate buffer. Fractions were pooled, desalted and freeze dried as in Example 10. Yield: 3.1 mg of a pale yellow solid, 70% by HPLC (215 nm area %); $C_{74}H_{102}N_{16}O_{26}$; FABMS m/z 1632 (M+H)$^+$, 1654 M+Na)$^+$, 1670 (M+K)$^+$; calc. for $C_{74}H_{103}N_{16}O_{26}$, 1631.72; $C_{74}H_{103}N_{16}O_{26}$, 1631.72; $C_{74}H_{102}N_{16}O_{26}$, Na, 1653.70; $C_{74}H_{102}N_{16}O_{26}$, K, 1669.68.

13) N-Decanoyl-L-β-(3-benzothienyl)alanyl-cyclodepsipeptide-2 (Compound 12)

A mixture of N-decanoyl-L-β-(3-benzothienyl)-alanine (0.072 g, 0.191 mmol), HOBT (0.030 g, 0.191 mmol) and DCC (0.039 g, 0.191 mmol) was dissolved in 0.47 mL DMF and stirred at RT for about 50 min (in situ activated ester solution). FMOC-cyclodepsipeptide-2 (7.4 mg, 0.005 mmol) was dissolved in 0.20 mL of DMF; two aliquots (0.050 mL total) of activated ester were added over time and the reaction was monitored by HPLC. After 85 min at RT the reaction mixture was diluted with about 2.8 mL MeOH containing about 21 mg of ammonium acetate. Product was isolated by size exclusion chromatography on a 25×85 mm column (Sephadex LH-20 fine, 11.6 g, swelled in MeOH); the sample solution was applied and eluted with MeOH at about 0.6 mL/min. Product-containing fractions (as determined by HPLC) were pooled and MeOH was removed under vacuum at 30° C. Product residue was not weighed.

The FMOC-protected product was deblocked as in Example 9. After 45 min at RT the reaction mixture was diluted with 2.0 mL of 0.4 M pH 7.2 buffer, 3.0 mL distilled water and 1.0 mL AcN. The product was isolated on an ENVI-Chrom-P 0.5 g cartridge as in Example 9; the product was eluted with about 29% $CH_3CN$, 0.06 M in pH 7.2 ammonium phosphate buffer. Fractions were pooled, desalted and freeze dried as in Example 10. Yield: 3.5 mg of a pale yellow solid, 67% by HPLC (215 nm area %); $C_{72}H_{100}N_{16}O_{26}S$; FABMS m/z 1638 (M+H)$^+$, 1660 (M+Na)$^+$, 1676 (M+K)$^+$; calc. for $C_{72}H_{101}N_{16}O_{26}S$, 1637.68; $C_{72}H_{100}N_{16}O_{26}SNa$, 1659.66; $C_{72}H_{100}N_{16}O_{26}SK$, 1675.64.

14) N-Hexadecylcarbamoyl-cyclodepsipeptide-2 (Compound 15)

FMOC-cyclodepsipeptide-2 (3.7 mg) was dissolved in 0.30 mL of potassium borate buffer (0.3 M borate, aqueous pH 8.8) in 75% MeOH, 0.003 mL of hexadecylisocyanate was added, the mixture ultrasonicated then vigorously stirred for 50 min at RT; 0.004 mL of the isocyanate was added, stirred at RT for 45 min then at 40° C. for 10 min. The reaction mixture was diluted with 2 mL of 0.4 M ammonium phosphate pH 7.2 buffer, 2 mL distilled water, 0.6 mL MeOH and 1 mL $CH_3CN$, then ultrasonicated and membrane filtered. The product was isolated on an ENVI-Chrom-P 0.5 g cartridge as in Example 9; product was eluted using 50% $CH_3CN$, 0.07 M in pH 7.2 buffer. Product-containing fractions were pooled, desalted and freeze dried as in Example 10; 6 mL of 80% AcN was used to elute the product. Yield: 3.2 mg of a pale yellow solid, 92% by HPLC (215 nm area %).

The FMOC-protected product (3.2 mg) was deblocked, isolated, desalted and freeze dried as in Example 10. Yield: 2.7 mg of a pale yellow solid, 93% by HPLC (215 nm area %); $C_{68}H_{106}N_{16}O_{25}$; FABMS m/z 1548 (M+H)$^+$, 1570 (M+Na)$^+$, 1586 (M+K)$^+$; calc. for $C_{68}H_{107}N_{16}O_{25}$, 1547.76; $C_{68}H_{106}N_{16}O_{25}Na$, 1569.74; $C_{68}H_{106}N_{16}O_{25}K$, 1585.72.

15) N-Dodecylcarbamoyl-L-β-(2-naphthyl)alanyl-cyclodepsipeptide-2 (Compound 16)

A mixture of N-dodecylcarbamoyl-L-β-(2-naphthyl) alanine (0.049 g, 0.114 mmol), HOBT (0.017 g, 0.114 mmol), and DCC (0.026 g, 0.114 mmol) was dissolved in 0.50 mL DMF and stirred at RT for about 30 min (in situ activated ester solution). FMOC-cyclodepsipeptide-2 (6.1 mg, 0.004 mmol) was dissolved in 0.20 mL DMF; two aliquots of activated ester were added over time and the reaction was monitored by HPLC. After 90 min at RT the reaction mixture was quenched and product was isolated on an ENVI-Chrom 0.5 g resin cartridge as in Example 9; product was eluted using 38% $CH_3CN$, 0.05 M in pH 7.2 buffer. The product-containing fractions were pooled, desalted and freeze dried as in Example 10. Yield: 3.9 mg of a pale yellow solid, 81% by HPLC (215 nm area %).

The FMOC-protected product (3.9 mg) was deblocked and the product was isolated on an ENVI-Chrom-P 0.5 g resin cartridge as in Example 9; the product was eluted with 33% $CH_3CN$, 0.04 M in pH 7.2 buffer. Fractions were pooled, desalted and freeze dried as in Example 10.

Yield: 2.7 mg of a pale yellow solid, 88% by HPLC (215 nm area %); $C_{87}H_{109}N_{17}O_{26}$; FABMS m/z 1688(M+H)$^+$, 1710(M+Na)$^+$; calc. for $C_{77}H_{110}N_{17}O_{26}$, 1688.78; $C_{77}H_{109}N_{17}O_{26}Na$, 1710.76.

16) N-Decanoyl-L-β-(2-naphthyl)alanyl-cyclodepsipeptide-2 (Compound 17)

A mixture of N-decanoyl-L-β-(2-naphthyl)-alanine (0.021 g, 0.057 mmol), HOBT (0.0095 g, 0.057 mmol) and diisopropylcarbodiimide (0.0081 mL, 0.057 mmol) was dissolved in 0.60 mL of methylene chloride and stirred at RT for about 30 min (in situ activated ester solution). FMOC-cyclodepsipeptide-2 (5.7 mg, 0.004 mmol) was dissolved in 0.20 mL of DMF; two aliquots (0.080 mL total) of the activated ester were added over time and the reaction was monitored by HPLC. After 105 min at RT the reaction mix was quenched and product was isolated as in Example 9. The product-containing peaks (determined by HPLC) were pooled, desalted and freeze dried as is Example 10. Yield: 5.8 mg of a pale yellow solid, about 90% by HPLC (264 nm area %); $C_{89}H_{112}N_{16}O_{28}$.

The FMOC-protected product (5.8 mg) was deblocked and isolated as in Example 12.

Yield: 3.9 mg of a pale yellow solid, about 86% by HPLC (215 nm area %); $C_{74}H_{102}N_{16}O_{26}$, MW 1630.72. FAB-MS m/z 1631 (M+H)$^+$, 1653 (M+Na)$^+$; $C_{74}H_{102}N_{16}O_{26}$; FABMS m/z 1631 (M+H)$^+$, 1653 (M+Na)$^+$; calc. for $C_{74}H_{103}N_{16}O_{26}$, 1631.72; $C_{74}H_{102}N_{16}O_{26}$, Na, 1653.70.

In the foregoing, methods of preparing intermediates and final products are presented in sufficient detail to enable one skilled in the art to practice the preferred and alternative embodiments of the invention hereof. Nevertheless, the invention is to be limited only by the following claims:

What is claimed is:

1. A method for preparing an intermediate for use in the synthesis of a lipodepsipeptide antibiotic, including the steps of:

(a) Obtaining an A21978 complex having a cyclic depsipeptide unit by fermentation of Streptomyces roseosporus;

(b) Protecting the orinithine amino group of the A21978 antibiotic complex by FMOC, the protective function 9-fluorenylmethoxycarbonyl;

(c) Treating the product from the reaction of step (b) with a deacylase enzyme to provide a single protected peptide; and (d) Using a modified Edman degradation method or peptidase enzymatic reactions to obtain a protected intermediate in the form of a cdpeptide chosen from the group consisting of FMOC-cdpeptide-2, FMOC-cdpeptide-1, or FMOC-cdpeptide, by reducing in size by one to three amino acids in the exocyclic tripeptide side chain of the cyclic depsipeptide unit of said complex.

2. The method according to claim 1, wherein, after step (d):

(e) chemically modifying a core FMOC cdpeptide to produce a protected anti-microbial derivative; and (f) Removing the protecting FMOC group to produce an antibiotic active against gram positive bacteria including strains of methicillin-resistant Staphylococcus aureus and vancomycin-resistant enterococci.

3. The method according to claim 1, wherein the intermediate of step (d) is designated the protected FMOC form of cdpeptide, cdpeptide-1, or cdpeptide-2, which is chemically modified to produce an anti-microbial derivative, per the following:

A) A-(X1)(X2)(X3)-cdpeptide

B) A-(X2)(X3)-cdpeptide

C) A-(X3)-cdpeptide

Wherein for Case A,) A-(X1)(X2)(X3)-cdpeptide

A=R'—(C=O)—, R'—SO$_2$—, R'—(C=NH)—, R'—(C=S)—, R'—NH—(C=S)—, R'—NH—(C=O)—, R'—O—(C=O)—, or R'CH$_2$—, where R' is alkyl, cycloalkyl, alkenyl, aryl, heteroaryl, or heterocyclic and X1 is an amino acid residue or peptide residue, X2 is L-asparginyl or another amino acid residue and X3 is L-aspartyl or another amino acid residue For case B) A-(X2)(X3)-cdpeptide "A" is the same as described for Case A) and X2 is L-asparaginyl or another amino acid residue and X3 is L-aspartyl or another amino acid residue For case C) A-(X3)-cdpeptide "A" is the same as described in Case A) and X3 is aspartyl or another amino acid residue.

4. An antibacterial compound prepared from a chemically derivatized protected form of cdpeptide, having the following structure, where Y equals FMOC or H:

A—X1—X2—X3—

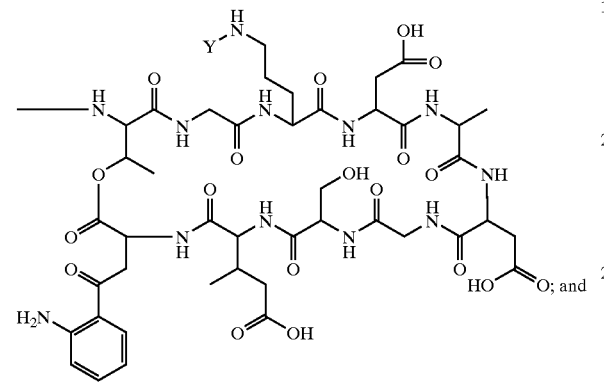

said compound is selected from a group consisting of the following or their corresponding salts:

| Cmp | A | X1 | X2 | X3 | Y |
|---|---|---|---|---|---|
| 1P | $CH_3(CH_2)_{11}NHCO$ | — | — | Asp | FMOC |
| 1 | $CH_3(CH_2)_{11}NHCO$ | — | — | Asp | H |
| 2 | $CH_3(CH_2)_{11}NHCO$ | — | Asn | Asp | FMOC |
| 3 | $CH_3(CH_2)_{11}NHCO$ | — | Asn | Asp | H |
| 4 | $CH_3(CH_2)_8CO$ | — | Asn | Asp | H |
| 4P | $CH_3(CH_2)_8CO$ | — | Asn | Asp | FMOC |
| 5 | $CH_3(CH_2)_8CO$ | L-Phe | Asn | Asp | H |
| 5P | $CH_3(CH_2)_8CO$ | L-Phe | Asn | Asp | FMOC |
| 6 | $CH_3(CH_2)_8CO$ | D-Phe | Asn | Asp | H |
| 6P | $CH_3(CH_2)_8CO$ | D-Phe | Asn | Asp | FMOC |
| 7 | $CH_3(CH_2)_9SO_2$ | L-Phe | Asn | Asp | H |
| 8 | $CH_3(CH_2)_9SO_2$ | L-Phe | Asn | Asp | FMOC |
| 9 | $CH_3(CH_2)_8CO$ | L-Kyn | Asn | Asp | H |
| 9P | $CH_3(CH_2)_8CO$ | L-Kyn | Asn | Asp | FMOC |
| 10 | $CH_3(CH_2)_8CO$ | D-Kyn | Asn | Asp | H |
| 10P | $CH_3(CH_2)_8CO$ | D-Kyn | Asn | Asp | FMOC |
| 11 | $CH_3(CH_2)_8CO$ | L-1-Naph | Asn | Asp | H |
| 11P | $CH_3(CH_2)_8CO$ | L-1-Naph | Asn | Asp | FMOC |
| 12 | $CH_3(CH_2)_8CO$ | L-Bthio | Asn | Asp | H |
| 12P | $CH_3(CH_2)_8CO$ | L-Bthio | Asn | Asp | FMOC |
| 13 | $CH_3(CH_2)_8CO$ | L-Harm | Asn | Asp | H |
| 13P | $CH_3(CH_2)_8CO$ | L-Harm | Asn | Asp | FMOC |
| 14 | $CH_3(CH_2)_8CO$ | D-Harm | Asn | Asp | H |
| 14P | $CH_3(CH_2)_8CO$ | D-Harm | Asn | Asp | FMOC |
| 15 | $CH_3(CH_2)_{15}NHCO$ | — | Asn | Asp | H |
| 15P | $CH_3(CH_2)_{15}NHCO$ | — | Asn | Asp | FMOC |
| 16 | $CH_3(CH_2)_{11}NHCO$ | L-2-Naph | Asn | Asp | H |
| 16P | $CH_3(CH_2)_{11}NHCO$ | L-2-Naph | Asn | Asp | FMOC |
| 17 | $CH_3(CH_2)_8CO$ | L-2-Naph | Asn | Asp | H |
| 17P | $CH_3(CH_2)_8CO$ | L-2-Naph | Asn | Asp | FMOC |

*Standard amino acid abbreviations with L-configuration except L-β-(3-benzothienyl)-alanine(L-Bthio); L-1,2,3,4-tetrahydronorharman-3-carboxylic acid (L-Harm); L-β-(1-naphthyl)-alanine (L-1-Naph); L-β-(2-naphthyl)-alanine (L-2-Naph) and where noted for D-configuration.

5. A protected cdpeptide intermediate designated protected cdpeptide, as represented in the following embodiment, and which can be used to synthesize a lipodepsipeptide antibiotic: H-protected cdpeptide; H-(X3)-protected cdpeptide; H-(X2)(X3)-protected cdpeptide, where, for all three cases H is hydrogen, X2 is asparaginyl, X3 is aspartyl and the protecting group is 9-fluorenylmethoxycarbonyl, designated FMOC; wherein the protected 9-fluorenylmethoxycarbonyl-cdpeptide, designated FMOC-cdpeptide, $C_{58}H_{72}N_{12}O_{21}$, has the structure:

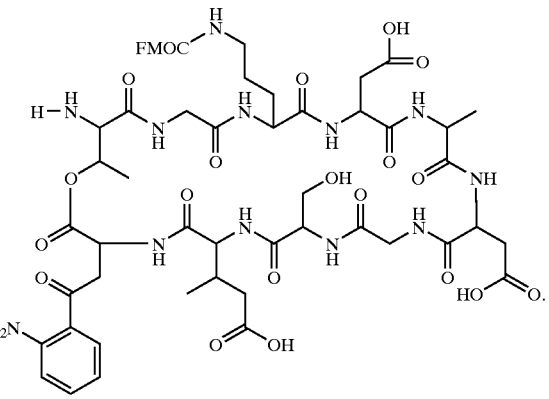

6. A protected cdpeptide intermediate designated protected cdpeptide-1, as represented in the following embodiment, and which can be used to synthesize a lipodepsipeptide antibiotic: H-protected cdpeptide H-(X3)-protected cdpeptide; H-(X2)(X3)-protected cdpeptide, where, for all three cases H is hydrogen, X2 is asparaginyl, X3 is aspartyl and the protecting group is 9-fluorenylmethoxycarbonyl, designated FMOC; wherein the protected 9-fluorenylmethoxycarbonyl-cdpeptide-1, designated FMOC-cdpeptide-1, $C_{62}H_{77}N_{13}O_{24}$, has the structure:

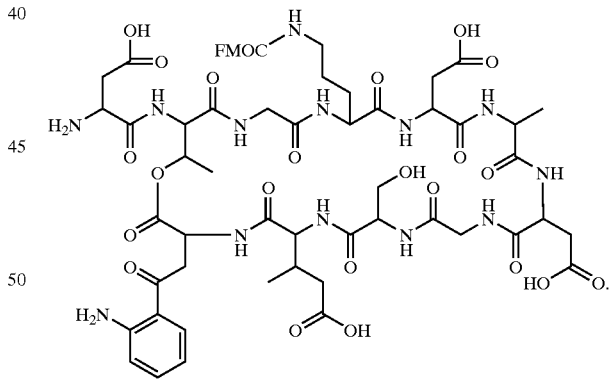

7. A protected cdpeptide intermediate designated protected cdpeptide-2, as represented in the following embodiment, and which can be used to synthesize a lipodepsipeptide antibiotic: H-protected cdpeptide H-(X3)-protected cdpeptide; H-(X2)(X3)-protected cdpeptide, where, for all three cases H is hydrogen, X2 is asparaginyl, X3 is aspartyl and the protecting group is 9-fluorenylmethoxycarbonyl, designated FMOC; wherein the protected 9-fluorenylmethoxycarbonyl-cdpeptide-2 designated FMOC-cdpeptide-2, $C_{66}H_{83}N_{15}O_{26}$, has the structure:

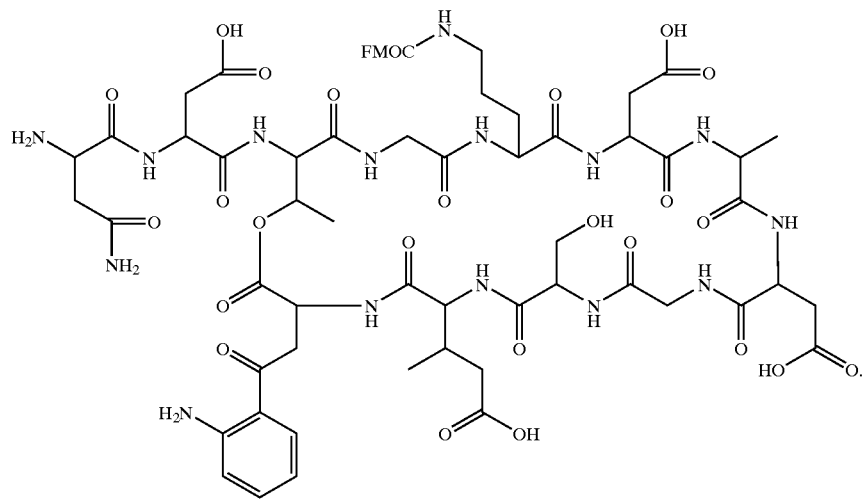

8. The method according to claim 3 wherein said amino acid residue is chosen for X1 from the group consisting of L-phenylalanyl, L-kynurenyl, L-β-(1-naphthyl)-alanyl, L-β-(2-naphthyl)-alanyl, L-β-(3-benzothienyl)-alanyl, L-1,2,3,4-tetrahydronorharman-3-carbonyl, L-β-(2-quinolyl)-alanyl, L-1,2,3,4-tetrahydroisoquinoline-3-carbonyl, and L-tryptophylglycyl.

9. A protected cdpeptide intermediate designated protected cdpeptide, as represented in the following embodiment, and which can be used to synthesize a lipodepsipeptide antibiotic, the protecting group being a solid phase support; and the protected solid phase support-cdpeptide has the structure:

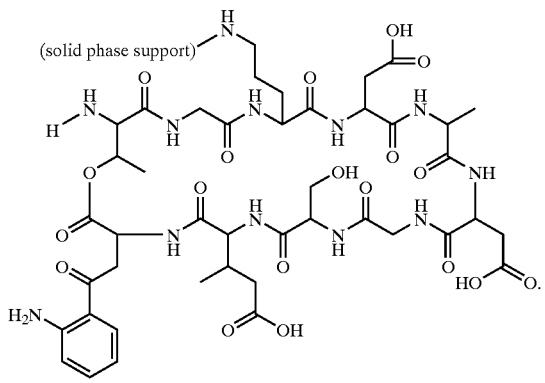

* * * * *